(12) United States Patent
Fearnot et al.

(10) Patent No.: US 7,655,033 B2
(45) Date of Patent: Feb. 2, 2010

(54) S-SHAPED STENT DESIGN

(75) Inventors: Neal E. Fearnot, West Lafayette, IN (US); Blayne A. Roeder, Lafayette, IN (US); Alan R. Leewood, Lafayette, IN (US); Jichao Sun, West Lafayette, IN (US)

(73) Assignee: Med Institute, Inc., West Lafayette, IN (US)

( * ) Notice: Subject to any disclaimer, the term of this patent is extended or adjusted under 35 U.S.C. 154(b) by 342 days.

(21) Appl. No.: 11/297,913

(22) Filed: Dec. 8, 2005

(65) Prior Publication Data

US 2006/0161243 A1 Jul. 20, 2006

Related U.S. Application Data

(60) Provisional application No. 60/634,814, filed on Dec. 9, 2004.

(51) Int. Cl.
*A61F 2/06* (2006.01)
(52) U.S. Cl. ..................................................... 623/1.15
(58) Field of Classification Search ................ 623/1.15, 623/1.18, 1.1, 1.17, 1.12
See application file for complete search history.

(56) References Cited

U.S. PATENT DOCUMENTS

| 4,580,568 | A | 4/1986 | Gianturco | 128/345 |
|---|---|---|---|---|
| 4,886,062 | A | 12/1989 | Wiktor | 128/343 |
| 5,015,253 | A | 5/1991 | MacGregor | 623/1 |
| 5,019,090 | A | 5/1991 | Pinchuk | 606/194 |
| 5,104,404 | A * | 4/1992 | Wolff | 623/1.16 |
| 5,133,732 | A | 7/1992 | Wiktor | 606/195 |
| 5,226,913 | A | 7/1993 | Pinchuk | 623/1 |
| 6,273,911 | B1 * | 8/2001 | Cox et al. | 623/1.15 |
| 6,336,937 | B1 * | 1/2002 | Vonesh et al. | 623/1.13 |
| 6,454,795 | B1 * | 9/2002 | Chuter | 623/1.15 |
| 6,719,782 | B1 * | 4/2004 | Chuter | 623/1.15 |
| 7,112,055 | B1 * | 9/2006 | Anukhin et al. | 425/365 |
| 2002/0049490 | A1 * | 4/2002 | Pollock et al. | 623/1.15 |
| 2003/0055485 | A1 * | 3/2003 | Lee et al. | 623/1.15 |
| 2003/0176914 | A1 * | 9/2003 | Rabkin et al. | 623/1.15 |
| 2003/0225449 | A1 * | 12/2003 | Denison | 623/1.15 |
| 2004/0158306 | A1 | 8/2004 | Mitelberg et al. | 623/1.2 |
| 2006/0116751 | A1 * | 6/2006 | Bayle et al. | 623/1.16 |
| 2006/0136031 | A1 * | 6/2006 | Gallo et al. | 623/1.11 |
| 2007/0032856 | A1 * | 2/2007 | Limon | 623/1.15 |
| 2007/0055349 | A1 * | 3/2007 | Santos et al. | 623/1.15 |
| 2007/0106369 | A1 * | 5/2007 | Brown et al. | 623/1.15 |

\* cited by examiner

*Primary Examiner*—Anhtuan T Nguyen
*Assistant Examiner*—Sarah A Simpson
(74) *Attorney, Agent, or Firm*—Brinks Hofer Gilson & Lione

(57) ABSTRACT

A variable curvature stent limb is disclosed herein. A stent derived from a plurality of these variable curvature stent limbs may be highly compressible, such that it is compatible with a low-profile delivery device. This stent may be useful over a wider range of body vessel diameters and may possess a greater fatigue life, since this stent may provide a more controlled constant radial force.

13 Claims, 4 Drawing Sheets

S-SHAPED STENT DESIGN

RELATED APPLICATIONS

This application claims priority to U.S. Provisional Application Ser. No. 60/634,814 filed Dec. 9, 2004. The disclosure of the priority application is incorporated by reference herein in its entirety.

BACKGROUND

A stent is an expandable prosthesis that can be delivered into a body vessel or passageways such as blood vessels, respiratory ducts, gastrointestinal ducts, urinary vessels, and the like. Stents have been employed to treat a host of diseases and disorders, including abdominal aortic aneurysms, coronary artery disease, and blockage of the bile duct. These devices are typically deployed in a compressed state using a catheter, of which there are many different types. In the case of arterial disease, a catheter can be guided through a patient's arterial system, until the catheter's distal end reaches a desired location within the patient, typically a constriction or lesion in an artery. Once the catheter is correctly positioned inside the artery, the stent can be released. During the deployment process the stent is converted from a compressed state to an expanded state that serves to provide support to and/or keep open the artery.

Stents can generally be divided into two types with regard to the manner in which they are converted from the compressed state to the expanded state. These groups are self-expanding stents and balloon expandable stents. Self-expanding stents, as the name suggests, will automatically expand from the compressed state to the expanded state when they are released from the catheter. Balloon expandable stents, on the other hand, are mounted on the exterior of a balloon that is located toward the distal end of the catheter. Conversion from the compressed state to the expanded state is achieved by inflating the balloon, which concomitantly expands the balloon expandable stent.

One drawback commonly associated with self-expanding stents is that they must be compressed from the expanded state to a compressed state so that they can be loaded into the catheter. Compressing these stents typically strains the stent and also creates radial force. The amounts of strain and radial force created will depend on the specific design of the stent, the materials from which the stent is constructed, and the extent to which the stent is compressed. In many cases, the amount of strain and the amount of radial force increase as the stent is compressed to smaller diameters. Eventually, the strain may become so severe that the stent will undergo permanent deformation or failure. As a result, this strain may limit the degree to which the stent can be compressed. Since the amount of radial force increases as the stent is compressed to smaller diameters, it becomes progressively more difficult to compress these stents to smaller diameters. Thus, it may be difficult to compress these stents to the desired diameter, especially when a smaller diameter is desired. Furthermore, the increased radial force makes it much more difficult to release the compressed stent from the catheter, since the amount of radial force present is directly proportional to the amount of friction that will occur between the compressed stent and the inside of the catheter.

Another problem with many of the current designs is that they have a short fatigue life. In terms of a stent, the fatigue life is the number of cycles of compression/expansion that the stent can undergo before it fails or permanently deforms. For example, arterial stents undergo cycling due to normal blood flow through a patient's blood vessels. With every heart beat, the heart creates a surge of blood that pulses through the blood vessels, causing them to expand. Once this surge of blood passes, the blood vessel contracts. Thus, the stent is continuously compressed and expanded. In many current stent designs, the stresses created by this cycling are focused at specific regions within the stent and consequently these regions are the first to permanently deform.

Ideally, a stent would be capable of more evenly distributing the strain associated with cycling over a greater area of the stent. This in turn should lower the peak magnitude of strain, resulting in a stent with a greater fatigue life. In addition, a stent capable of more evenly distributing the strain associated with cycling over a greater area of the stent should be capable of being compressed to fit within a low-profile catheter. Furthermore, an ideal stent would have a wide range of use, in that it would be capable of being used for a range of diameters.

BRIEF SUMMARY

In one aspect of the invention, there is a variable curvature stent limb that has a first variably curved region that is attached to an inner region, where the first variably curved region has a first radius of curvature that varies along the length thereof. In addition, the first radius of curvature is non-constant. The variably curvature stent limb also possesses a second variably curved region that is attached to an inner region, where the second variably curved region has a second radius of curvature that varies along the length thereof. In addition, the second radius of curvature is non-constant. Furthermore, the first variably curved region and the second variably curved region face in opposite directions.

DETAILED DESCRIPTION OF THE DRAWINGS AND THE PRESENTLY PREFERRED CONFIGURATIONS

A variable curvature stent limb is disclosed herein. A stent derived from a plurality of these variable curvature stent limbs may be highly compressible, such that it is compatible with a low-profile delivery device. This stent may be useful over a range of body vessel diameters and may also possess an enhanced fatigue life.

Figure 1A:
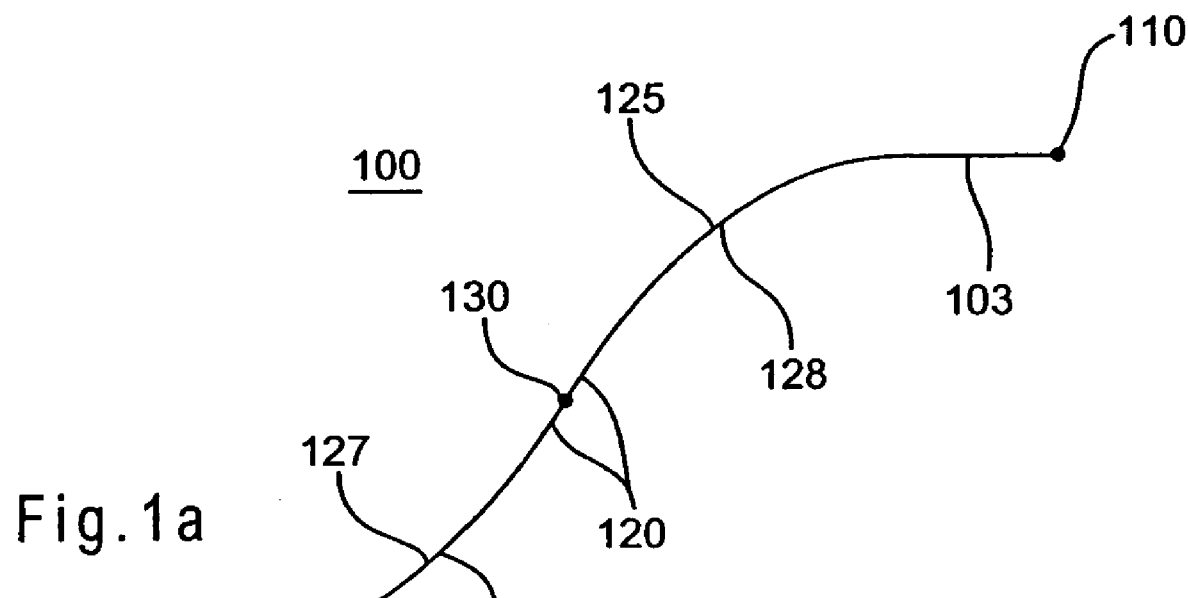
FIG. 1a illustrates a longitudinal cross-sectional view of a variable curvature stent limb with a first straight region and a second straight region.
Figure 1B:
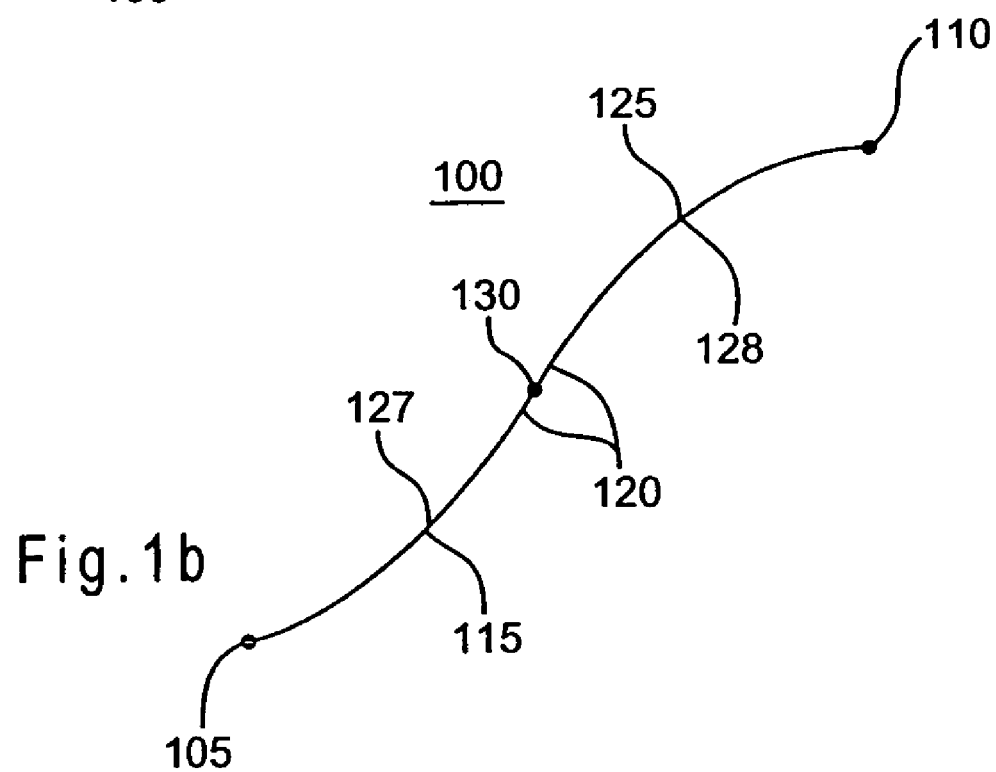
FIG. 1b illustrates a longitudinal cross-sectional view of a variable curvature stent without a first straight region and without a second straight region.

FIG. 1a illustrates a longitudinal cross-sectional view of a variable curvature stent limb 100 with a first straight region 102 and a second straight region 103. FIG. 1b illustrates a longitudinal cross-sectional view of a variable curvature stent 100 without the first straight region 102 and without the second straight region 103. The stent limb 100 may be defined by a first end 105 and a second end 110. The first straight region 102 may begin at the first end 105 and may be connected to a first variably curved region 115. The first curved region 115 may in turn be connected to an inner region 120. The inner region 120 may serve to connect the first curved region 115 with a second variably curved region 125. The inner region 120 may be straight or curved and may extend along a length between the first and second curved regions 115 and 125 or may constitute a point contact therebetween. The second curved region 125 may be connected to the second straight region 103, where the second straight region 103 terminates at the second end 110. In one configuration, the first curved region 115 and the second curved region 125 may be concave. In another configuration, the first curved region 115 and the second curved region 125 may each face opposite directions.

The first curved region 115 and the second curved region 125 may have a first radius of curvature 127 and a second radius of curvature 128, respectively. The first radius of curvature 127 and the second radius of curvature 128 may be non-constant, such that the first radius of curvature 127 and the second radius of curvature 128 vary over the length of the curved regions 115 and 125, respectively. In one configuration, the first radius of curvature 127 and the second radius of curvature 128 may be the same. In another configuration, the first radius of curvature 127 and the second radius of curvature 128 may be different.

The inner region 120 may include a midpoint 130, which is located equidistant from the first end 105 and the second end 110. In one configuration, the stent limb 100 may be symmetrical around the midpoint 130. For example, the curved regions 115 and 125 may have identical length and curvature and the straight regions 105 and 125 may be of equal length. When the first curved region 115 and the second curved region 125 face opposite directions, the midpoint 130 may represent a point of inversion.

The various components of the limb 100 may be altered to affect the mechanical properties of the limb 100. For example, in one configuration the length of the straight regions 102 and 103 may be altered in unison. Alternatively, the length of the straight regions 102 and/or 103 may be altered individually. In another configuration, as shown in FIG. 1b, the straight regions 105 and 125 may not be present. In this case, the first curved region 115 begins at the first end 105 and the second curved region 125 terminates at the second end 110. In a further configuration, the length and/or curvature of the curved regions 115 and 125 may be altered, in unison or individually. In an additional configuration, the length of the inner region 120 may be altered. In another configuration, the inner region 120 may not be present so that the first curved region 115 and the second curved region 125 are connected directly to each other. In one configuration, the stent limb 100 may consist merely of the first curved region 115 and the second curved region 125, where the first curved region 115 and the second curved region 125 are connected at the midpoint 130.

The material from which the stent limb 100 is constructed may also affect the mechanical properties of the stent limb 100. The stent limb 100 may be made of any deformable biocompatible material, such as polymeric materials, metals or ceramic materials. In one configuration, the stent limb 100 may be made of an elastic plastic metal, such as stainless steel. In another configuration, the stent limb 100 may be made of super elastic material, such as a shape memory alloy. Shape memory alloys may include nitinol. In another configuration, the stent limb 100 may be made from a combination of materials.

A variety of methods may be employed to manufacture the stent limb 100 as described herein. For example, the stent limb 100 may be formed by cutting the stent limb 100 from a sheet or a cannula. The cutting procedure may be achieved using a variety of techniques, including a laser. In another example, the stent limb 100 may be formed by bending a wire or ribbon into the shape desired for stent limb 100. In a further example, the stent limb 100 may be formed by determining the desired shape of the stent limb 100 computationally and building a form such that the ribbon or wire may be pressed into the desired shape. Alternatively, the ribbon or wire may be shaped by applying a load such that the ribbon or wire acquires the desired shape. A plurality of stent limbs 100 may be assembled to form a circular or tubular stent 195. See FIG. 7. A variety of methods may be employed to join the stent limb 100 to another stent limb 100. These methods include laser welding, fusion welding, soldering or even utilizing biocompatible epoxies. In another example, the entire stent 195 may be manufactured from a sheet or cannula, using a laser for example.

Figure 7:
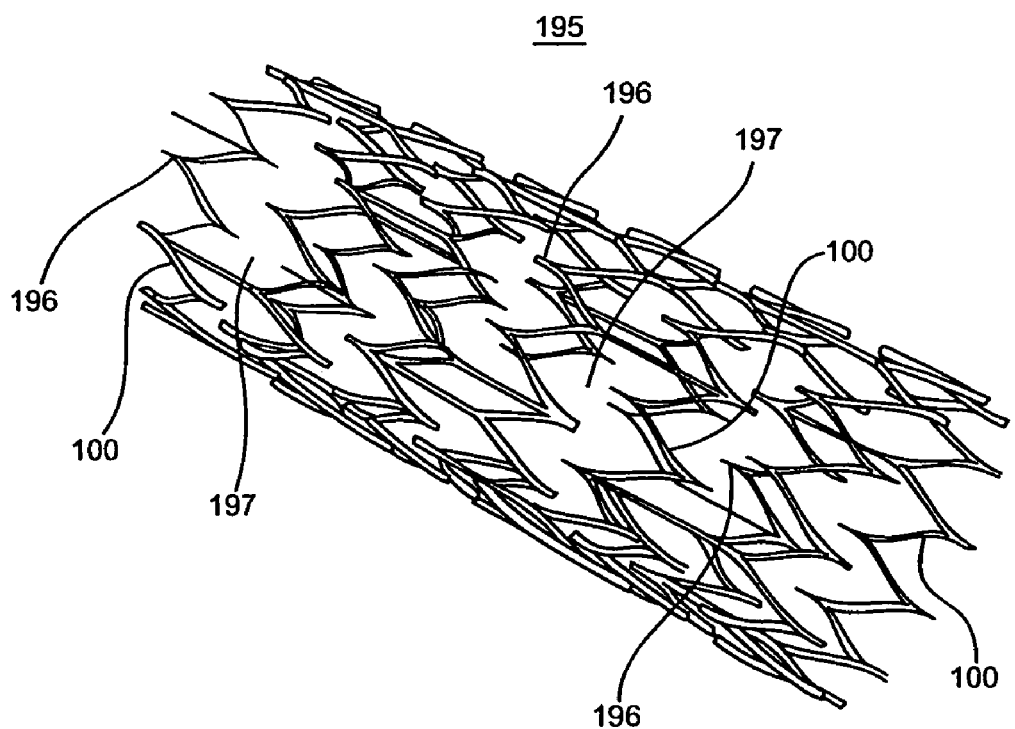
FIG. 7 illustrates a plurality of variable curvature stent limbs assembled in a pattern to create a stent.

In another example, the stent 195, as shown in FIG. 7, may be formed by attaching a plurality of flat segments end to end such that the stent 195 is assembled in a fully compressed state. In the case of most common super elastic materials, the stent 195 may be expanded over successive mandrels to achieve the appropriate size and then stress relieved. This process of expanding the stent 195 over successive mandrels may then provide the plurality of stent limbs 100 comprising the stent 195 with the desired shape.

Figures 2A, 2B, 2C:
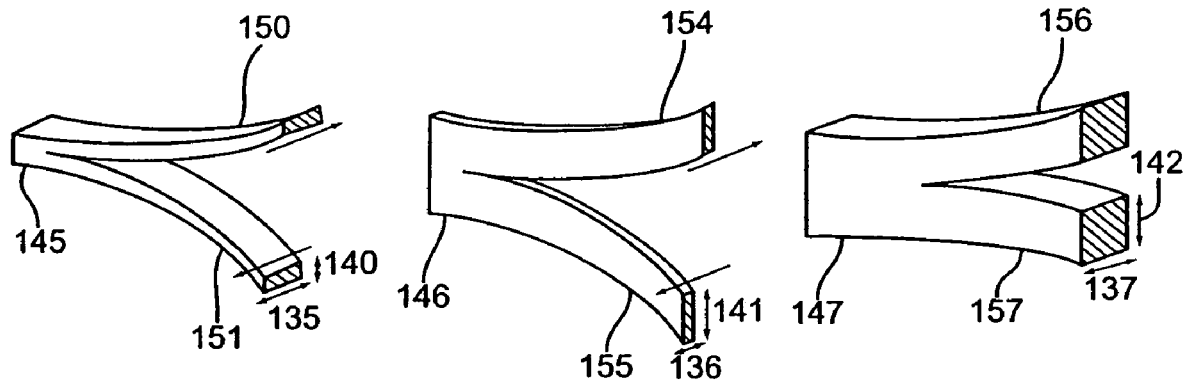
FIGS. 2a, 2b and 2c illustrate longitudinal 3-dimensional views of three configurations of a variable curvature stent limb connection.

FIG. 2a illustrates a longitudinal 3-dimensional view of a stent limb connection 145. FIG. 2b illustrates a longitudinal 3-dimensional view of a stent limb connection 146. In one configuration, as shown in FIG. 2a, a first stent limb 150 may be attached to a second stent limb 151 via the stent limb connection 145. Furthermore, the stent limbs 150 and 151 may have a thickness 135 and a width 140. In a preferred configuration, as shown in FIG. 2a, the thickness 135 is greater than the width 140. In another configuration, as shown in FIG. 2b, a first stent limb 154 may be attached to a second stent limb 155 via the stent limb connection 146. Furthermore, the stent limbs 154 and 155 may have a width 141 and a thickness 136, where the width 141 is greater than the thickness 136. In another configuration, as shown in FIG. 2c, a first stent limb 156 may be attached to a second stent limb 157 via the stent limb connection 147. Furthermore, the stent limbs 156 and 157 may have a width 142 and a thickness 137, where the width 142 is the same as the thickness 137.

When the stent limbs 154 and 155 are compressed together, the limbs 154 and 155 may be more likely to overlap than the stent limbs 150 and 151, since the thickness 136 is smaller than the width 141 in the stent limbs 154 and 155. This in turn may cause a variety of problems in a stent employing a plurality of stent limbs 154 and 155. For example, such a stent may experience permanent deformation or out of plain buckling and/or twisting. However, the stent limbs 150 and 151 may be less likely to overlap upon compression, since increasing the thickness 135 in comparison to the width 140 may make it more difficult for the limbs 150 and 151 to pass over one another during compression. This in turn may reduce or prevent the occurrence of permanent deformation or out of plane buckling and/or twisting in a stent employing a plurality of limbs 150 and 151.

In one configuration, the thickness 135 and the width 140 may be altered to affect the mechanical response or behavior of the stent limb 100. For example, it may be desirable to vary the thickness 135 and the width 140 over the length of the limb 100.

Figure 3:
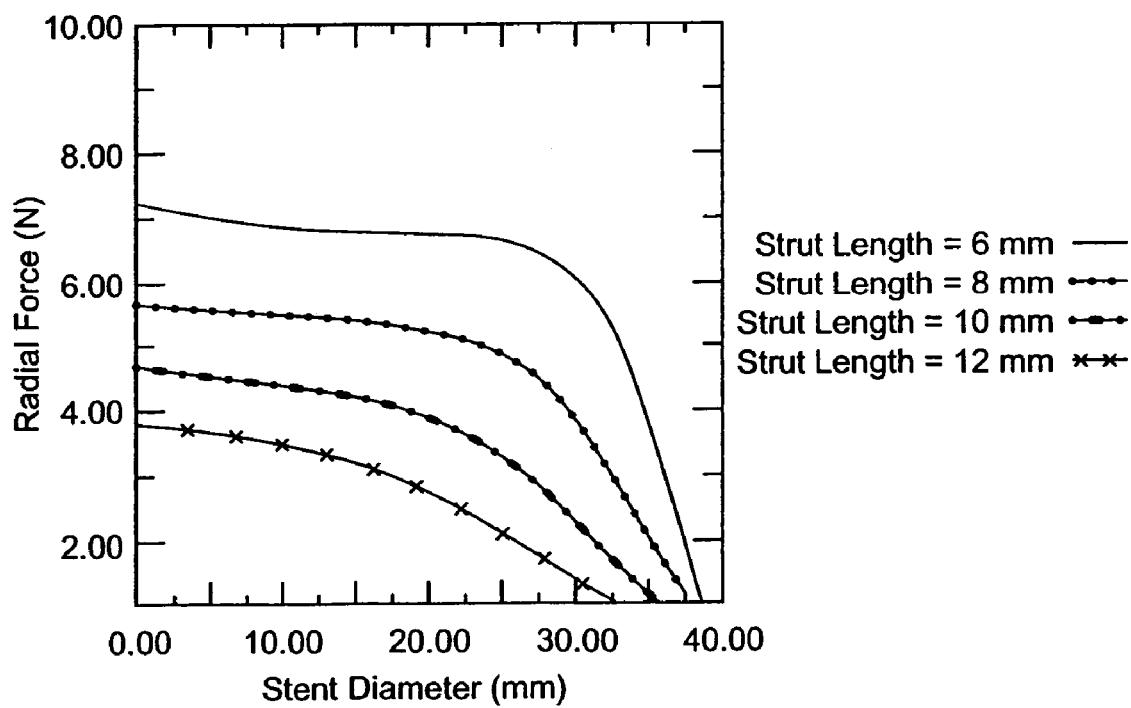
FIG. 3 demonstrates how changes in the length of a variable curvature stent limb influence the corresponding radial force curve.

FIG. 3 demonstrates how changes in the length of the variable curvature stent limb may influence the corresponding radial force curve. Radial force curves, as discussed herein, provide a graphical comparison of the radial force (N) on the y-axis versus the stent diameter (mm) on the x-axis. Thus, the radial force curve indicates how much force is necessary to compress a stent to a given stent diameter. The radial force curves can also be interpreted as providing the amount of radial force that a stent will possess at a given stent diameter. In some cases, the radial force curve may have a radial force plateau. As used herein, a radial force plateau signifies a substantially constant radial force that exists over a range of stent diameters and appears as a nearly flat or horizontal region on the radial force curve. In some cases, the radial force plateau may be broader, in which case it exists over a wider range of stent diameters, as compared to the radial force curve of another stent. A stent with a broad radial force plateau may be capable of being used for a wider range of diameters (i.e., diameters falling anywhere within the diameter range of the plateau).

The radial force plateau may also vary in magnitude. For example, a higher or greater magnitude indicates that the corresponding stent has a plateau at a higher radial force, as compared to another stent. In fact, a higher magnitude radial force plateau may indicate that the corresponding stent may provide better sealing and support characteristics than a stent with a lower magnitude radial force plateau.

FIG. 3 reveals that a decrease in the length of the stent limb 100 increases the magnitude of the radial force and causes a more pronounced plateau. FIG. 3 provides radial force curves for four different stent limbs 100, where each of the limbs varies in length. The radial force curves provided in FIG. 3 correspond to stent limb lengths of 6 mm, 8 mm, 10 mm and 12 mm. Decreasing the length of the stent limb drives the stresses higher, such that stress induced martensite may occur. Thereby, resulting in a desirable flattening of the radial force curve.

Figure 4:
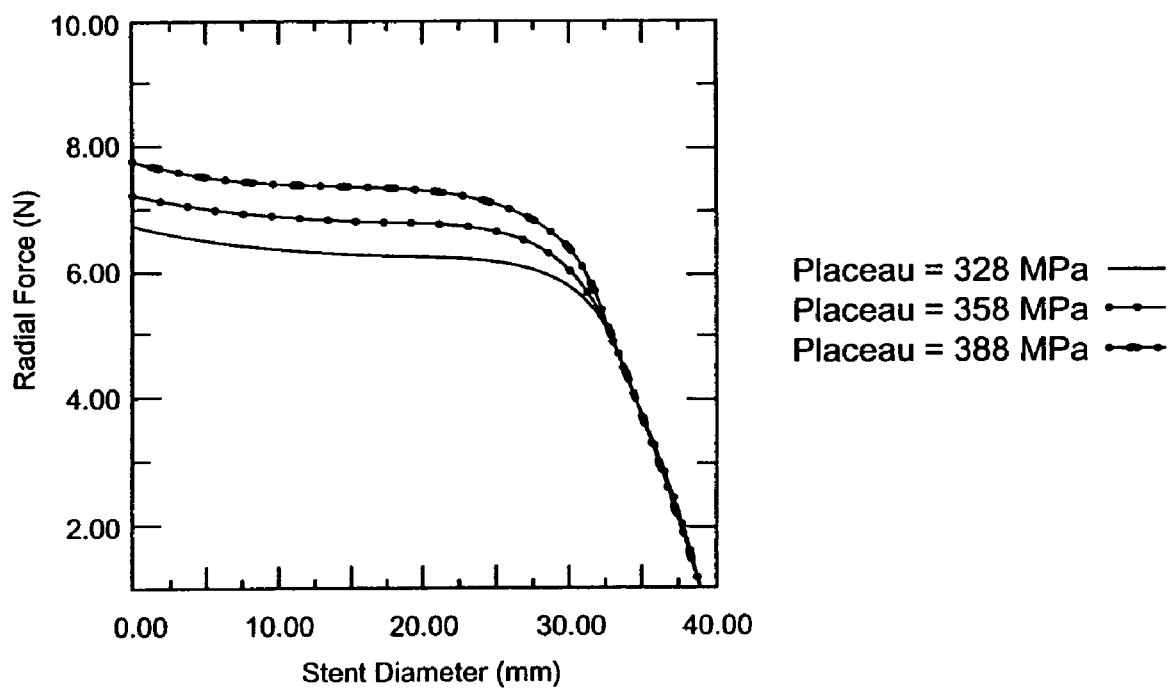
FIG. 4 demonstrates how changes in the plateau stress of a super-elastic material, such as a shape memory alloy, may alter the radial force curve of a variable curvature stent limb.
Figure 5A:
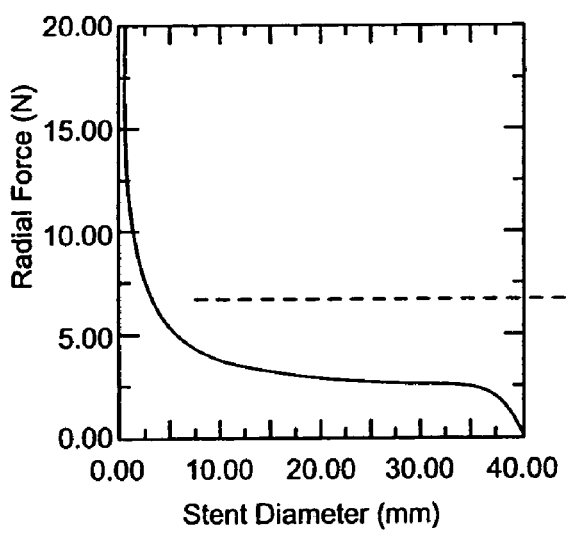
FIG. 5a provides a radial force diagram for a stent employing an equal radius stent limb.
Figure 5B:
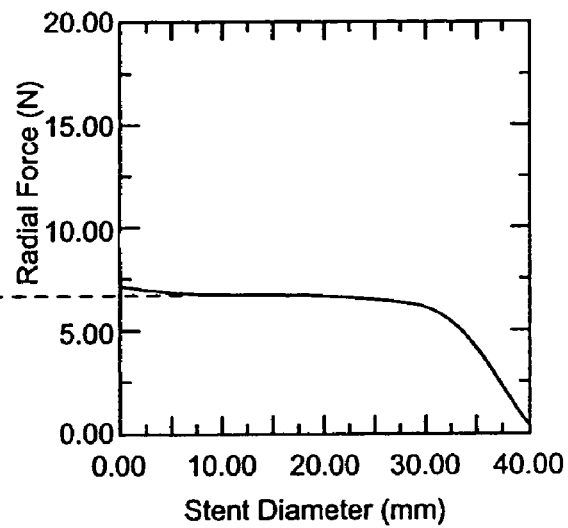
FIG. 5b provides a radial force diagram for a stent employing a variable curvature stent limb.

FIG. 4 demonstrates how changes in the plateau stress of a super elastic material, such as a shape memory alloy, may alter the radial force curve. FIG. 4 provides radial force curves corresponding to three different stent limbs 100. Each of these stent limbs 100 are composed of nitinol, where the nitinol in each of the stent limbs 100 has a different plateau stress. The radial force curves correspond to stent limbs 100 with plateau stresses of 328 MPa, 358 MPa and 388 MPa. As the plateau stress of the stent limb 100 increases, the radial force plateaus also increase. This may be used to optimize the design of a stent depending on the radial force that is desired FIG. 5a provides a radial force diagram for a stent employing an equal radius stent limb. FIG. 5b provides a radial force diagram for a stent employing a stent limb 100 possessing a variable curvature. A comparison of the two figures reveals that the equal radius stent limbs provide a radial force curve in which the plateau is narrower, since it extends over a smaller range of diameters (FIG. 5a) than the variable curvature stent limbs 100 (FIG. 5b). Furthermore, the equal radius stent limbs provide a radial force curve that is of a lower magnitude (FIG. 5a) than the variable curvature stent limbs 100 (FIG. 5b). FIG. 5a also reveals that at progressively smaller stent diameters, the equal radius stent limbs generate a steep increase in radial force, compared to the variable curvature stent limbs 100. Thus, after the stent of FIG. 5a is compressed to a stent diameter of approximately 5.0 mm, further compression to a smaller diameter necessitates a nearly exponential increase in the amount of radial force required. The variable curvature stent limbs 100, on the other hand, do not require a substantial increase in force to compress the stent diameter to stent diameters well below 5.0 mm. As a result, the variable curvature stent limbs 100 should result in lower interfacial forces between the stent 195 (see FIG. 7) comprising a plurality of stent limbs 100 and a delivery device used to deploy the stent 195, resulting in decreased frictional forces between the stent 195 and the delivery device. The reduction in interfacial forces should concomitantly lower the amount of force necessary to deploy the stent 195, which may aid in the accurate delivery of the stent 195.

Figure 6:
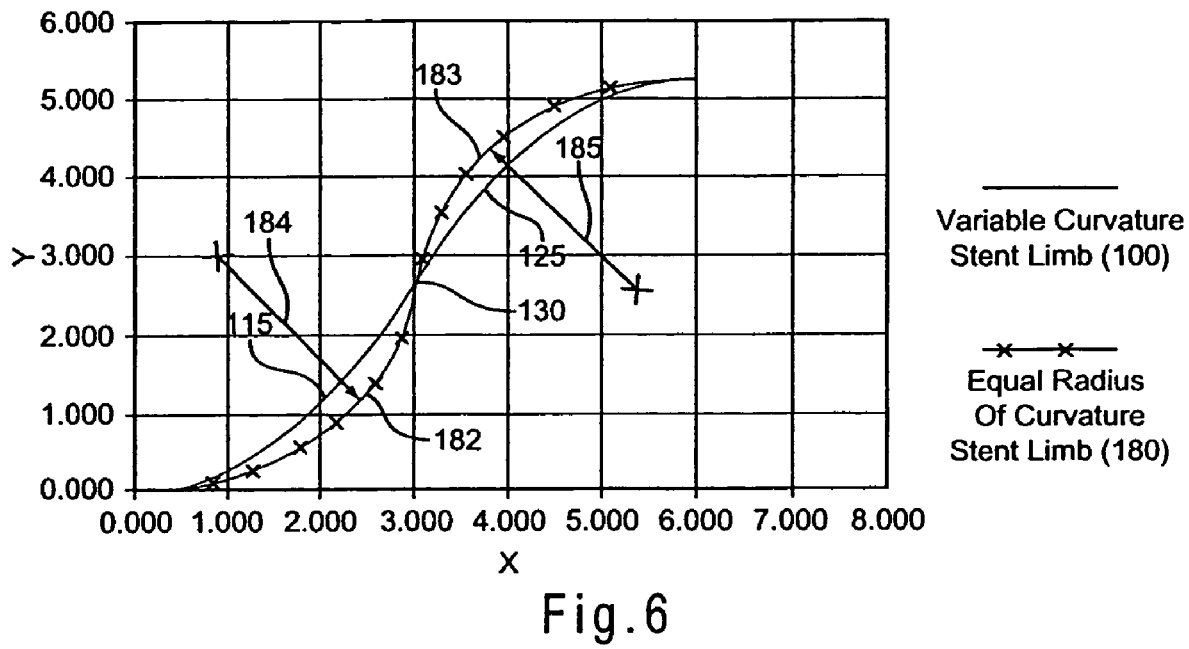
FIG. 6 illustrates the shape of a variable curvature stent limb compared to an equal radius of curvature stent limb.

FIG. 6 illustrates the shape of the variable curvature stent limb 100 compared to an equal radius of curvature stent limb 180. The equal radius of curvature stent limb 180 may have a first curved region 182 and a second curved region 183. The equal radii of curvature of the curved regions 182 and 183 are illustrated by a radius of curvature 184 and a radius of curvature 185, respectively. The curved regions 115 and 125 of the stent limb 100, as well as the curved regions 182 and 183 of the stent limb 180, may both face in opposite directions. In each case the stent limbs 100 and stent limb 180 may also have a midpoint point 130, where the midpoint 130 serves as an inversion point between the two curved regions 115 and 125, as well as the curved regions 182 and 183. As show in FIG. 6, the curved regions 115 and 125 may be shallower or less concave than the curved regions 182 and 183.

FIG. 7 illustrates a plurality of variable curvature stent limbs 100, where the plurality of stent limbs 100 are assembled in a pattern to create the stent 195. The stent limbs 100 are attached via a plurality of stent limb connections 196. In addition, the stent 195 may have a plurality of open cells 197, wherein the open cells 197 provide space between the stent limbs 100 such that the stent 195 can be compressed. Although FIG. 7 depicts the stent limbs 100 assembled in one pattern, the stent limbs 100 may also be assembled in a variety of other patterns as well.

It is therefore intended that the foregoing detailed description be regarded as illustrative rather than limiting, and that it be understood that it is the following claims, including all equivalents, that are intended to define the spirit and scope of this invention.

The invention claimed is:

1. A stent having a plurality of variable curvature stent limbs comprising:
   a first variably curved region attached to an inner region, the first variably curved region comprising a first curvature that is non-constant along the length thereof and that includes no linear portions;
   a second variably curved region attached to the inner region, the second variably curved region comprising a second curvature that is non-constant along the length thereof and that includes no linear portions;
   wherein the first variably curved region and the second variably curved region face in opposite directions, the first variably curved region and the second variably curved region having the same curvature at any locations a given distance from a first point of attachment of the first variably curved region to the inner region and a second point of attachment of the second variably curved region to the inner region;

the first variably curved region and the second variably curved region are concave;

the first non-constant curvature being less concave than an imaginary constant radius curve extending from a first end of the first variably curved region to a second end;

the second non-constant curvature being less concave than an imaginary constant radius curve extending from a first end of the second variably curved region to a second end; and wherein each of the plurality of variable curvature stent limbs are connected end to end and curve away from each other in an undulating pattern having a substantially cylindrical structure when the stent is in an expanded state, such that when the stent is compressed the first and second variably curved regions of circumferentially adjacent variable curvature stent limbs flex toward each other and exert an outward radial force, and wherein a radial force plateau exerted by the stent limbs is established at stent diameters larger than 5 mm and the radial force plateau remains substantially constant for all diameters from substantially compressed to 5 mm.

2. The stent of claim 1 wherein the variable curvature stent limbs further comprise a width and a thickness, wherein the thickness is greater than the width.

3. The stent of claim 1 wherein the variable curvature stent limbs further comprise a width and a thickness, wherein the width and the thickness are the same.

4. The stent of claim 1 wherein the variable curvature stent limbs further comprise a first straight region attached to the first variably curved region and a second straight region attached to the second variably curved region.

5. The stent of claim 4, wherein the first straight region and the second straight region of the variable curvature stent limbs have the same length.

6. The stent of claim 1 wherein the inner region of the variable curvature stent limbs further comprises a midpoint about which the first variably curved region and the second variably curved region are symmetrical.

7. The stent of claim 6 wherein the variable curvature stent limbs further comprise a width and a thickness, wherein the thickness is greater than the width.

8. The stent of claim 6 wherein the variable curvature stent limbs further comprise a width and a thickness, wherein the width and the thickness are the same.

9. The stent of claim 6 wherein the inner region of the variable curvature stent limbs is a point where the first and second variably curved regions are directly connected to each other.

10. The stent of claim 1 wherein the first variably cured region and the second variably curved region of the variable curvature stent limbs are made from a shape memory alloy.

11. The stent of claim 10, wherein the shape memory alloy is nitinol.

12. The stent of claim 1, wherein the variable curvature stent limbs have a width that is substantially constant along an entire length thereof.

13. The stent of claim 1, wherein the variable curvature stent limbs have a thickness that is substantially constant along an entire length thereof.

* * * * *

UNITED STATES PATENT AND TRADEMARK OFFICE
CERTIFICATE OF CORRECTION

PATENT NO. : 7,655,033 B2 Page 1 of 1
APPLICATION NO. : 11/297913
DATED : February 2, 2010
INVENTOR(S) : Fearnot et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 378 days.

Signed and Sealed this

Twenty-third Day of November, 2010

David J. Kappos
*Director of the United States Patent and Trademark Office*